(12) United States Patent
Zoller et al.

(10) Patent No.: US 7,709,513 B2
(45) Date of Patent: May 4, 2010

(54) BENZOOXAZOL-2-ONE DERIVATIVES AS LIPASE AND PHOSPHOLIPASE INHIBITORS

(75) Inventors: Gerhard Zoller, Frankfurt am Main (DE); Stefan Petry, Frankfurt am Main (DE); Gunter Müller, Frankfurt am Main (DE); Hubert Heuer, Frankfurt am Main (DE); Norbert Tennagels, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/950,960

(22) Filed: Dec. 5, 2007

(65) Prior Publication Data

US 2008/0167355 A1 Jul. 10, 2008

Related U.S. Application Data

(63) Continuation of application No. PCT/EP2006/005097, filed on May 27, 2006.

(30) Foreign Application Priority Data

Jun. 9, 2005 (DE) ........................ 10 2005 026 808

(51) Int. Cl.
  *A61K 31/423* (2006.01)
  *C07D 263/58* (2006.01)
(52) U.S. Cl. ...................... 514/375; 548/221
(58) Field of Classification Search ................. 514/375; 548/221
  See application file for complete search history.

(56) References Cited

U.S. PATENT DOCUMENTS

| 4,988,719 | A  | * | 1/1991 | Wagner et al. .............. 514/369 |
| 2008/0161370 | A1 | * | 7/2008 | Zoller et al. ................. 514/367 |

FOREIGN PATENT DOCUMENTS

| EP | 0463944 | 1/1992 |
| EP | 0768305 | 4/1997 |
| FR | 1469297 | 2/1967 |
| WO | WO 01/57002 | 8/2001 |
| WO | WO 2004/035550 | 4/2004 |
| WO | WO 2004/094393 | 11/2004 |
| WO | WO 2004/094394 | 11/2004 |

OTHER PUBLICATIONS

Botella et al., Aminolyse de carbamates cycliques analogues de la carboxybiotine; catalyse metallique et modelisation de transfert de carboxyle, 1992, Tetrahedron, vol. 48, Issue 24, p. 5111 (abstract).*
Ayupova, A., et, al., Synthesis of Some 3-Acylbenzoxazolinones, O'Zbekiston Kimyo Jurnali, vol. 2, pp. 30-33 (2000)—Abstract from Chemical Abstracts.
Nachman, R. J., et. al., 3-(1-Imidazoyl)-6-Methoxy-2-Benzoxalinone, Journal of Heterocyclic Chemistry, vol. 22, (1985), pp. 279-280.
Zinner, H., et. al., Benzazoles. IV. Mannich Bases of Benzoxazolone, Chemische Berichte, vol. 89, pp. 2131-2136, (1956)—Abstract from Chemical Abstracts.

* cited by examiner

Primary Examiner—Kamal A Saeed
Assistant Examiner—Kristin Bianchi
(74) Attorney, Agent, or Firm—Barbara E. Kurys

(57) ABSTRACT

The invention relates to benzooxazol-2-one derivatives of general formula (I) with the meanings indicated in the description, the pharmaceutically usable salts thereof, and the use thereof as medicinal substances.

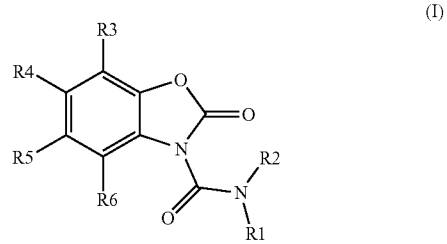

17 Claims, No Drawings

BENZOOXAZOL-2-ONE DERIVATIVES AS LIPASE AND PHOSPHOLIPASE INHIBITORS

This application is a continuation of International application No. PCT/EP2006/005,097, filed May 27, 2006, which is incorporated herein by reference in its entirety; which claims the benefit of priority of German Patent Application No. 102005026808.0, filed Jun. 9, 2005.

The present invention relates to benzooxazol-2-one derivatives of the general formula I, to their pharmaceutically useful salts and to their use as medicinal substances.

Benzooxazolone derivatives of similar structure are described in DE 3102907, FR1469297. However, these are used as pesticides and fungicides.

Compounds having an inhibitory effect on hormone-sensitive lipase are described in the prior art for example in WO2004/035550, WO2005/073199 or WO03/051842. Compounds with an inhibitory effect on endothelial lipase are described in the prior art for example in WO2004/094394, WO2004/094393.

It is an object of the present invention to provide alternative compounds which have an inhibitory effect on hormone-sensitive lipase or endothelial lipase.

The invention relates to benzooxazol-2-one derivatives of the general formula I

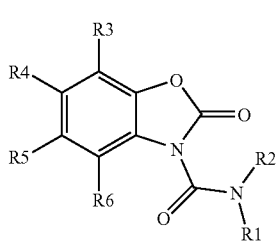

in which the meanings are:
R1 $(C_5-C_{16})$-alkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_3-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl, aminosulfonyl;
R2 hydrogen, $(C_1-C_6)$-alkyl; or
R1 and R2 form together with the nitrogen atom bearing them a monocyclic, saturated or partially unsaturated 4- to 7-membered ring system or a bicyclic saturated or partially unsaturated 8- to 14 membered ring system, of which individual members of the ring systems may be replaced by one to three atoms or atomic groups from the series —CHR8-, —CR8R8a-, —(C=R8)-, —NR9-, —C(=O)—, —O—, —S—, —SO—, —SO₂—, with the proviso that two units from the series —O—, —S—, —SO—, —SO₂— may not be adjacent;
R3, R4, R5, R6 independently of one another hydrogen, halogen, $(C_1-C_6)$-alkyl, $(C_1-C_3)$-alkyloxy-$(C_1-C_3)$-alkylene, hydroxy, $(C_1-C_6)$-alkylmercapto, amino, $(C_1-C_6)$-alkylamino, di-$(C_2-C_{12})$-alkylamino, $(C_1-C_6)$-alkylcarbonyl, COOR7, trifluoromethyl, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10 or unsubstituted or mono- or poly-F-substituted $(C_1-C_6)$-alkyloxy;
with the proviso that not more than one of the substituents R3, R4, R5 or R6 is halogen;
and with the proviso that not more than one of the substituents R3, R4, R5 or R6 is $(C_1-C_6)$-alkyl;
R7 hydrogen, $(C_1-C_6)$-alkyl, benzyl;
R8, R8a independently of one another $(C_1-C_6)$-alkyl, halogen, trifluoromethyl, COOR7, cyclopropyl, cyclopropylene;
R9, R10 independently of one another hydrogen, $(C_1-C_6)$-alkyl, —$(C_6-C_{10})$-aryl, $(C_5-C_{12})$-heteroaryl, $(C_3-C_{12})$-cycloalkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_4-C_{12})$-cycloalkyl, $(C_8-C_{14})$-bicycle;

the tautomeric forms of the compounds and the physiologically tolerated salts thereof.

Preferred compounds of the formula I are those in which
R1 is $(C_6-C_{12})$-alkyl, $(C_1-C_3)$-alkylene-$(C_6-C_{10})$-aryl, $(C_1-C_3)$-alkylene-$(C_5-C_{12})$-heteroaryl, $(C_1-C_3)$-alkylene-$(C_4-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;
R2 is hydrogen, $(C_1-C_6)$-alkyl; or
R1 and R2 together with the nitrogen atom bearing them are a monocyclic, saturated 5- to 6-membered ring system or a bicyclic saturated or partially unsaturated 9- to 10-membered ring system, of which individual members of the ring systems may be replaced by one to three atoms or atomic groups from the series —CHR8-, —CR8R8a-, —(C=R8)-, —NR9-, —O—, —S—, with the proviso that two units from the series —O—, —S— may not be adjacent;
R3, R4, R5, R6 are independently of one another hydrogen, $(C_1-C_3)$-alkyloxy-$(C_1-C_3)$-alkylene, hydroxy, mono-$(C_1-C_6)$-alkylaminocarbonyl, di-$(C_2-C_8)$-alkylaminocarbonyl, COOR7, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, $(C_1-C_6)$-alkylcarbonyl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10;
R7 is hydrogen, $(C_1-C_6)$-alkyl, benzyl;
R8, R8a are independently of one another $(C_1-C_6)$-alkyl, halogen, trifluoromethyl, COOR7, cyclopropyl, cyclopropylene;
R9, R10 are independently of one another hydrogen, $(C_1-C_6)$-alkyl, $(C_6-C_{10})$-aryl, $(C_5-C_{12})$-heteroaryl, $(C_3-C_{12})$-cycloalkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_4-C_{12})$-cycloalkyl.

Preferred compounds of the formula I are also those in which
R1 is $(C_6-C_{12})$-alkyl, $(C_1-C_3)$-alkylene-$(C_6-C_{10})$-aryl, $(C_1-C_3)$-alkylene-$(C_5-C_{12})$-heteroaryl, $(C_1-C_3)$-alkylene-$(C_4-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;
R2 is hydrogen, $(C_1-C_6)$-alkyl; or
R1 and R2 together with the nitrogen atom bearing them are a monocyclic, saturated 5- to 6-membered ring system or a bicyclic saturated or partially unsaturated 9- to 10 membered ring system, of which individual members of the ring systems may be replaced by one to three atoms or atomic groups from the series —CHR8-, —CR8R8a-, —(C=R8)-, —NR9-, —O—, —S—, with the proviso that two units from the series —O—, —S— may not be adjacent;

R3, R4, R5, R6 are independently of one another hydrogen, $(C_1-C_3)$-alkyloxy-$(C_1-C_3)$-alkylene, hydroxy, COOR7, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, $(C_1-C_6)$-alkylcarbonyl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10;

R7 is hydrogen, $(C_1-C_6)$-alkyl, benzyl;

R8, R8a are independently of one another $(C_1-C_6)$-alkyl, halogen, trifluoromethyl, COOR7, cyclopropyl, cyclopropylene;

R9, R10 are independently of one another hydrogen, $(C_1-C_6)$-alkyl, $(C_6-C_{10})$-aryl, $(C_1-C_4)$-alkylene-$(C_6-C_{10})$-aryl.

Particularly preferred compounds of the formula I are those in which

R1 is $(C_6-C_{12})$-alkyl, benzyl, $(C_1-C_3)$-alkylene-$(C_5-C_{12})$-heteroaryl, $(C_1-C_3)$-alkylene-$(C_4-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;

R2 is hydrogen; or

R1 and R2 together with the nitrogen atom bearing them are a monocyclic, saturated 5- to 6-membered ring system or a bicyclic saturated or partially unsaturated 9- to 10-membered ring system, of which individual members of the ring systems may be replaced by one to three atoms or atomic groups from the series —CHR8-, —CR8R8a-, —(C=R8)-, —NR9-, —O—, —S—, with the proviso that two units from the series —O—, —S— may not be adjacent;

R3, R4, R5, R6 are independently of one another hydrogen, hydroxy, COOR7, $(C_1-C_6)$-alkylsulfonyl, aminosulfonyl, pentafluorosulfanyl, phenyl, $(C_1-C_6)$-alkylcarbonyl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10;

R7 is hydrogen, $(C_1-C_6)$-alkyl;

R8, R8a are independently of one another $(C_1-C_6)$-alkyl, halogen, trifluoromethyl, COOR7, cyclopropyl;

R9, R10 are independently of one another hydrogen, $(C_1-C_6)$-alkyl.

A further particularly preferred embodiment is compounds of the formula I in which R3, R6 is hydrogen, R4 or R5 is not hydrogen.

Further preferred compounds of the formula I are those in which

R1 and R2 together with the nitrogen atom bearing them form a monocyclic, saturated 5- to 6-membered ring system, of which individual members of the ring systems may be replaced by one to two atoms or atomic groups from the series —CHR8-, —NR9-, in which R8 is as defined above, and R9 is $(C_1-C_6)$-alkyl or cyclopropyl.

A further particularly preferred embodiment is compounds of the formula I in which R2 is hydrogen.

Very particularly preferred compounds of the formula I are those in which

R1 is $(C_6-C_{12})$-alkyl, benzyl, —CH$_2$—$(C_5-C_{12})$-heteroaryl, $(C_8-C_{14})$-bicycle, where benzyl, heteroaryl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;

R2 is hydrogen;

R3 is hydrogen;

R4, R5 are independently of one another hydrogen, hydroxy, mono-$(C_1-C_6)$-alkylaminocarbonyl, di-$(C_2-C_8)$-alkylaminocarbonyl, COOR7, $(C_1-C_6)$-alkylsulfonyl, aminosulfonyl, phenyl, $(C_1-C_6)$-alkylcarbonyl, O—CO—NR9R10, O—CO—$(C_1-C_6)$-alkylene —CO—O—$(C_1-C_6)$-alkyl, O—CO—$(C_1-C_6)$-alkylene-CO—OH, O—CO—$(C_1-C_6)$-alkylene-CO—NR9R10;

R6 is hydrogen.

Particularly preferred compounds of the formula I are those in which

R1 is $(C_7-C_{12})$-alkyl, benzyl, $(C_1-C_3)$-alkylene-$(C_5-C_{12})$-heteroaryl, $(C_1-C_3)$-alkylene-$(C_4-C_{12})$-cycloalkyl, $(C_8-C_{14})$-bicycle, where benzyl, heteroaryl, cycloalkyl or bicycle may be substituted by halogen, $(C_1-C_6)$-alkyl, $(C_1-C_3)$-alkyloxy or trifluoromethyl;

R2 is hydrogen.

Further very particularly preferred compounds of the formula I are those in which R1 is $(C_6-C_{12})$-alkyl or benzyl, where benzyl may be substituted one or more times by $(C_1-C_6)$-alkyl;

R2 is hydrogen;

R3 is hydrogen;

R4, R5 are independently of one another hydrogen, halogen or $(C_1-C_6)$-alkylcarbonyl;

R6 is hydrogen.

Very particularly preferred compounds of the formula I are also those in which

R1 is benzyl, $(C_1-C_3)$-alkylene-$(C_5-C_{12})$-heteroaryl, $(C_1-C_3)$-alkylene-$(C_4-C_{12})$-cycloalkyl, —$(C_8-C_{14})$-bicycle, where benzyl, heteroaryl, cycloalkyl or bicycle may be substituted by halogen, $(C_1-C_6)$-alkyl, $(C_1-C_3)$-alkyloxy or trifluoromethyl;

R2 is hydrogen.

The invention relates to compounds of the formula I in the form of their salts, racemates, racemic mixtures and pure enantiomers, and to their diastereomers and mixtures thereof.

The alkyl radicals in the substituents R1, R2, R3, R4, R5, R6, R7, R8, R8a, R9 and R10 may be either straight-chain or branched. Halogen is fluorine, chlorine, bromine or iodine, in particular fluorine or chlorine.

Aryl means an aromatic carbocyclic mono- or bicyclic ring system which comprises 6 to 10 atoms in the ring or in the rings.

Heteroaryl is a mono- or bicyclic aromatic ring system having 5 to 12 ring members, in which at least one atom in the ring system is a heteroatom from the series N, O and S.

Suitable "heteroaryl rings" or "heteroaryl radicals" are, for example, benzimidazolyl, benzofuranyl, benzothiophenyl, benzoxazolyl, benzthiazolyl, benztriazolyl, benztetrazolyl, benzisoxazolyl, benzisothiazolyl, quinolinyl, furyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl, thiophenyl.

The heteroaryl rings or heteroaryl radicals may be substituted one or more times by suitable groups.

A cycloalkyl radical is a ring system which comprises one or more rings and which is in saturated or partially unsaturated (with one or two double bonds) form and which is composed exclusively of carbon atoms.

Bicycle means bicyclic ring systems which are in saturated or partially unsaturated form and which, apart from carbon, may also comprise one or more heteroatoms such as, for example, nitrogen, oxygen or sulfur. This definition also includes ring systems which comprise a fused benzene nucleus. Examples which may be mentioned are the tetrahydronaphthyl, alpha- or beta-tetralon-, indanyl- or indan-1-on-yl radical. Preferred bicyclic radicals are those of formula Ic

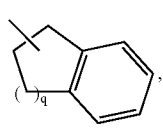

Ic with q=1 or 2.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention of the formula I, for example an ester, which on administration to a mammal such as, for example, a human is able to form (directly or indirectly) a compound of the formula I or an active metabolite thereof.

Physiologically functional derivatives also include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

The compounds of the invention of the general formula I in which the meanings are:

R1 $(C_5-C_{16})$-alkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_3-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl, aminosulfonyl;

R2 hydrogen, $(C_1-C_6)$-alkyl; or

R1 and R2 form together with the nitrogen atom bearing them a monocyclic, saturated or partially unsaturated 4- to 7-membered ring system or a bicyclic saturated or partially unsaturated 8- to 14 membered ring system, of which individual members of the ring systems may be replaced by one to three atoms or atomic groups from the series —CHR8-, —CR8R8a-, —(C=R8)-, —NR9-, —C(=O)—, —O—, —S—, —SO—, —SO$_2$—, with the proviso that two units from the series —O—, —S—, —SO—, —SO$_2$— may not be adjacent;

R3, R4, R5, R6 independently of one another hydrogen, halogen, $(C_1-C_6)$-alkyl, $(C_1-C_3)$-alkyloxy-$(C_1-C_3)$-alkylene, hydroxy, $(C_1-C_6)$-alkylmercapto, amino, $(C_1-C_6)$-alkylamino, di-$(C_2-C_{12})$-alkylamino, $(C_1-C_6)$-alkylcarbonyl, COOR7, trifluoromethyl, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10 or unsubstituted or mono- or poly-F-substituted $(C_1-C_6)$-alkyloxy;

R7 hydrogen, $(C_1-C_6)$-alkyl, benzyl;

R8, R8a independently of one another $(C_1-C_6)$-alkyl, halogen, trifluoromethyl, COOR7, cyclopropyl, cyclopropylene;

R9, R10 independently of one another hydrogen, $(C_1-C_6)$-alkyl, —$(C_6-C_{10})$-aryl, $(C_5-C_{12})$-heteroaryl, $(C_3-C_{12})$-cycloalkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_4-C_{12})$-cycloalkyl, $(C_8-C_{14})$-bicycle;

the tautomeric forms of the compounds and the physiologically tolerated salts thereof have a surprising inhibitory effect on hormone sensitive lipase, HSL, an allosteric enzyme in adipocytes which is inhibited by insulin and is responsible for the breakdown of fats in fat cells and thus for transferring fat constituents into the blood stream. Inhibition of this enzyme is therefore equivalent to an insulin-like effect of the compounds of the invention, eventually leading to a reduction of free fatty acids in the blood and of blood glucose. They can therefore be employed for metabolic derangements such as, for example, for non-insulin-dependent diabetes mellitus, for diabetic syndrome and for direct pancreatic damage.

The compounds of the invention of the general formula I, especially those in which R2 is hydrogen, may additionally have an inhibitory effect on endothelial lipase (EL). The preferred substrate for EL is HDL, which has antiatherosclerotic activity. A reduction in the HDL level leads to progression of atherosclerosis and its sequelae such as coronary heart disease and moreover favors development of the metabolic syndrome and its sequelae diabetes. An inhibition of EL should thus generally lead to prevention of atherosclerotic disorders and indirectly reduce the probability of people with an increased risk for diabetes becoming ill.

It has further been found that the inhibitory effect of the compounds of the invention of the general formula I is selective in relation to other lipases.

The compounds of the invention of the formula I may also have an inhibitory effect on triglyceride lipase.

Compounds of this type are particularly suitable for the treatment and/or prevention of
1. —Disorders of fatty acid metabolism and glucose utilization disorders
2. —Disorders of the insulin sensitivity of myo-, adipo- and hepatocytes (insulin resistance)-metabolic syndrome
3. Diabetes mellitus, especially type 2 diabetes, including the prevention of the sequelae associated therewith.
    Particular aspects in this connection are
        hyperglycemia,
        improvement in insulin resistance,
        improvement in glucose tolerance,
        protection of the pancreatic β cells
        prevention of macro- and microvascular disorders
4. Dyslipidemias and the sequelae thereof such as, for example, atherosclerosis, coronary heart disease, cerebrovascular disorders etc., especially those (but not restricted thereto) which are characterized by one or more of the following factors:
    high plasma triglyceride concentrations, high postprandial plasma triglyceride concentrations
    low HDL cholesterol concentration
    low apoA lipoprotein concentrations
    high LDL cholesterol concentrations
    small dense LDL cholesterol particles
    high apoB lipoprotein concentrations
5. Various other conditions which may be associated with the metabolic syndrome, such as:
    obesity (excess weight), including central obesity
    thromboses, hypercoagulable and prothrombotic stages (arterial and venous)
    high blood pressure
    heart failure such as, for example (but not restricted thereto), following myocardial infarction, hypertensive heart disease or cardiomyopathy
6. Other disorders or conditions in which inflammatory reactions or cell differentiation may for example be involved are:
    atherosclerosis such as, for example (but not restricted thereto), coronary sclerosis including angina pectoris or myocardial infarction, stroke
    vascular restenosis or reocclusion
    chronic inflammatory bowel diseases such as, for example, Crohn's disease and ulcerative colitis
    pancreatitis
    other inflammatory states
    retinopathy
    adipose cell tumors
    adipose cell carcinomas such as, for example, liposarcoma
    solid tumors and neoplasms such as, for example (but not restricted thereto), carcinomas of the gastrointestinal tract, of the liver, of the biliary tract and of the pancreas, endocrine tumors, carcinomas of the lungs, of the kidneys and of the urinary tract, of the genital tract, prostate carcinomas etc.
    acute and chronic myeloproliferative disorders and lymphomas
    angiogenesis
    neurodegenerative disorders
    Alzheimer's disease
    multiple sclerosis
    Parkinson's disease
    erythemato-squamous dermatoses such as, for example, psoriasis
    acne vulgaris
    other skin disorders and dermatological conditions which are modulated by PPAR
    eczemas and neurodermatitis
    dermatitis such as, for example, seborrheic dermatitis or photodermatitis
    keratitis and keratosis such as, for example, seborrheic keratoses, senile keratoses, actinic keratosis, photo-induced keratoses or keratosis follicularis
    keloids and keloid prophylaxis
    warts, including condylomata or condylomata acuminata
    human papilloma viral (HPV) infections, such as, for example, venereal papillomata, viral warts such as, for example, molluscum contagiosum, leukoplakia
    papular dermatoses such as, for example, lichen planus
    skin cancer such as, for example, basal cell carcinoma, melanomas or cutaneous T-cell lymphomas
    localized benign epidermal tumors such as, for example, keratoderma, epidermal naevi
    chilblains
    high blood pressure
    syndrome X
    polycystic ovary syndrome (PCOS)
    asthma
    osteoarthritis
    lupus erythematosus (LE) or inflammatory rheumatic disorders such as, for example, rheumatoid arthritis
    vasculitis
    wasting (cachexia)
    gout
    ischemia/reperfusion syndrome
    acute respiratory distress syndrome (ARDS)

Compounds which inhibit endothelial lipase are particularly suitable for the treatment and/or prevention of
1. Dyslipidemias and general impairments of lipid metabolism and their sequelae such as, for example, atherosclerosis, coronary heart disease, cerebrovascular disorders etc., especially those (but not restricted thereto) which are characterized by one or more of the following factors:
    high plasma triglyceride concentrations, high postprandial plasma triglyceride concentrations,
    low HDL cholesterol concentration
    low ApoA lipoprotein concentrations
    high LDL cholesterol concentrations
    small dense LDL cholesterol particles
    high ApoB lipoprotein concentrations
2. Various other conditions which may be associated with the metabolic syndrome, such as:
    obesity (excess weight), including central obesity
    thromboses, hypercoagulable and prothrombotic stages (arterial and venous)
    high blood pressure
    heart failure such as, for example (but not restricted thereto), following myocardial infarction, hypertensive heart disease or cardiomyopathy
    diabetes mellitus, in particular type 2 diabetes including the prevention of the sequelae associated therewith (hyperglycemia, glucose intolerance, loss of pancreatic β cells, macro- and microvascular disorders
3. Other disorders or conditions in which inflammatory reactions or cell differentiation may for example be involved are:

atherosclerosis such as, for example (but not restricted thereto), coronary sclerosis including angina pectoris or myocardial infarction, stroke vascular restenosis or reocclusion chronic inflammatory bowel diseases such as, for example, Crohn's disease and ulcerative colitis pancreatitis other inflammatory states retinopathy adipose cell tumors adipose cell carcinomas such as, for example, liposarcomas solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.

acute and chronic myeloproliferative disorders and lymphomas angiogenesis neurodegenerative disorders Alzheimer's disease multiple sclerosis Parkinson's disease erythemato-squamous dermatoses such as, for example, psoriasis acne vulgaris other skin disorders and dermatological conditions which are modulated by PPAR eczemas and neurodermatitis dermatitis such as, for example, seborrheic dermatitis or photodermatitis keratitis and keratoses such as, for example, seborrheic keratoses, senile keratoses, actinic keratosis, photo-induced keratoses or keratosis follicularis keloids and keloid prophylaxis warts, including condylomata or condylomata acuminata human papilloma viral (HPV) infections such as, for example, venereal papillomata, viral warts such as, for example, molluscum contagiosum, leukoplakia papular dermatoses such as, for example, lichen planus skin cancer such as, for example, basal-cell carcinomas, melanomas or cutaneous T-cell lymphomas localized benign epidermal tumors such as, for example, keratoderma, epidermal naevi chilblains high blood pressure syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequelae thereof.

The compounds of the formula I with R2 hydrogen are distinguished by favorable effects on disorders of lipid metabolism. They beneficially influence the HDL to LDL ratio and increase in particular the HDL level and are suitable for the prevention and treatment of dyslipidemias and metabolic syndrome and their diverse sequelae such as atherosclerosis, coronary heart disease, heart failure, obesity and diabetes.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2003. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S. The orally effective hypoglycemic active ingredients include, preferably, the sulfonylureas which act on the ATP-dependent potassium channel of the beta cells (e.g. disclosed in WO 97/26265 and WO 99/03861), biguanides, meglitinides, glucagon antagonists, oral GLP-1 agonists, DPP-IV inhibitors, insulin sensitizers, e.g. PPAR and PXR modulators and active ingredients such as, for example, oxadiazolidinediones, thiazolidinediones, inhibitors of liver enzymes which are involved in stimulating gluconeogenesis and/or glycogenolysis, modulators of glucose uptake such as, for example, glucosidase inhibitors, compounds which alter lipid metabolism and lead to a change in the blood lipid composition, compounds which reduce food intake or food uptake.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I are administered in combination with an active ingredient which acts on the ATP-dependent potassium channel of the beta cells, such as, for example, sulfonylureas (e.g. tolbutamide, glibenclamide, glipizide, glimepiride) or glinides (e.g. repaglinide).

In one embodiment, the compounds of the formula I are administered in combination with a biguanide such as, for example, metformin.

In one embodiment, the compounds of the formula I are administered in combination with a PPARgamma agonist or thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment, the compounds of the formula I are administered in combination with compounds with an inhibitory effect on SGLT-1 and/or 2, as disclosed directly or indirectly for example in WO2004/007517, WO2004/052902, WO2004/052903 and WO2005/121161.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol resorption inhibitor as described for example in WO 02/50027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6)). Caromax is a carob-containing product from Nutrinova, Nutrition Specialties & Food Ingredients GmbH, Industriepark Hoechst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (tesaglitazar, (S)-3-(4-[2-(4-methanesulfonyloxyphenyl) ethoxy]-phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine. In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[((4-aminoquinazolin-2-ylamino)methyl] cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c] pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol- 1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In another embodiment, the further active ingredient is a cannabinoidi receptor 1 antagonist (such as, for example, rimonabant, SR147778 or those as are described in, for example, EP 0656354, WO 00/15609, WO 02/076949, WO2005080345, WO2005080328, WO2005/080343, WO2005/075450, WO2005/080357, WO2001/70700, WO2003/026647-48, WO2003/02776, WO2003/040107, WO2003/007887, WO2003/027069, U.S. Pat. No. 6,509,367, WO2001/32663, WO2003/086288, WO2003/087037, WO2004/048317, WO2004/058145, WO2003/084930, WO2003/084943, WO2004/058744, WO2004/013120, WO2004/029204, WO2004/035566, WO2004/058249, WO2004/058255, WO2004/058727, WO2004/069838, US2004/0214837, US2004/0214855, US2004/0214856, WO2004/096209, WO2004/096763, WO2004/096794, WO2005/000809, WO2004/099157, US2004/0266845, WO2004/110453, WO2004/108728, WO2004/000817, WO2005/000820, US2005/0009870, WO2005/00974, WO2004/111033-34, WO2004/11038-39, WO2005/016286, WO2005/007111, WO2005/007628, US2005/0054679, WO2005/027837, WO2005/028456, WO2005/063761-62, WO2005/061509, WO2005/077897);

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds of the invention of the formula I was tested in the following enzyme assay systems:

1. HSL Inhibition Assay 1.1. Preparation of the Partially Purified HSL:

Isolated rat fat cells are obtained from epididymal adipose tissue from untreated male rats (Wistar, 220-250 g) by collagenase treatment in accordance with published methods (e.g. S. Nilsson et al., Anal. Biochem. 158, 1986, 399-407; G. Fredrikson et al., J. Biol. Chem. 256, 1981, 6311-6320; H. Tornquist et al., J. Biol. Chem. 251, 1976, 813-819). The fat cells from 10 rats are washed three times by flotation with 50 ml of homogenization buffer (25 ml Tris/HCl, pH 7.4, 0.25 M sucrose, 1 mM ETDA, 1 mM DTT, 10 µg/ml leupeptin, 10 µg/ml antipain, 20 µg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.) and suspended in 2.5 ml of 20 mM Tris/HCl, pH 7.0, 1 mM EDTA, 65 mM NaCl, 13% sucrose, 1 mM DTT, 10 µg/ml leupeptin/pepstatin/antipain. The suspension is dialyzed against 25 mM Tris/HCl, pH 7.4, 50% glycerol, 1 mM DTT, 10 µg/ml leupeptin, pepstatin, antipain at 4° C. overnight and then loaded onto a hydroxiapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at −70° C. for 4 to 6 weeks.

1.2 HSL Activity Assay:

To prepare the substrate, 25-50 µCi of [3H]trioleoylglycerol (in toluene), 6.8 µmol of unlabeled trioleoylglycerol and 0.6 mg of phospholipids (phosphatidylcholine/phosphatidylinositol 3:1 w/v) are mixed, dried with $N_2$ and then taken up in 2 ml of 0.1 M KPi (pH 7.0) by ultrasound treatment (Branson 250, microtip, setting 1-2, 2×1 min with an interval of 1 min). After addition of 1 ml of KPi and renewed ultrasound treatment (4×30 sec on ice with intervals of 30 sec), 1 ml of 20% BSA (in KPi) is added (final concentration of trioleoylglycerol 1.7 mM). For the reaction, 100 µl of substrate solution are pipetted into 100 µl of HSL solution (HSL prepared as above, diluted in 20 mM KPi, pH 7.0, 1 mM EDTA, 1 mM DTT, 0.02% BSA, 20 µg/ml pepstatin, 10 µg/ml leupeptin) and incubated at 37° C. for 30 min. Addition of 3.25 ml of methanol/chloroform/heptane (10:9:7) and of 1.05 ml of 0.1 M $K_2CO_3$, 0.1 M boric acid (pH 10.5) is followed by thorough mixing and finally centrifugation (800×g, 20 min). After phase separation, one equivalent of the upper phase (1 ml) is removed and the radioactivity is determined by liquid scintillation measurement.

1.3 Evaluation of the HSL-Inhibitory Effect:

Substances are normally tested in four independent mixtures. The inhibition of the HSL enzymatic activity by a test substance is determined by comparing with an uninhibited control reaction. The $IC_{50}$ is calculated from an inhibition plot with at least 10 concentrations of the test substance. The GRAPHIT, Elsevier-BIOSOFT software package is used to analyze the data.

2. EL Inhibition Assay:

2.1. Preparation of EL

EL is released as secretory protein in high concentration into cell culture medium (conditioned medium) by recombinant cell lines (CHO, HEK293). This is employed as enzyme solution after concentration.

2.2. EL Activity Assay

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates the fluorescent dye Bodipy which can be detected after separation by thin-layer chromatography on an HPTLC plate (silica gel 60, Merck) or directly in the reaction vessel by measuring the fluorescence.

The substrate solution is prepared by taking up 100 μg of 1,2-bis(4,4-difluoro-5,7-dimethyl-4-bora-3a,4a-diaza-s-indacene-3-undecanoyl)-sn-glycero-3-phospho-choline (manufacturer Molecular Probes), 2.4 mg of tripalmitin (Sigma) and 7.9 mg of DOP-choline (1,2-dioleoyl-sn-glycero-3-phosphocholine) in 393 μl of chloroform and then transferring 157 μl into a fresh reaction vessel. After evaporation of the solvent, the lipid mixture is dissolved in 4 ml of 200 mM TRIS-HCl, 150 mM sodium chloride, pH=7.4, by sonication twice. The subsequent enzymic reaction takes place at 37° C. for 60 minutes. For this purpose, 45 μl of the substrate solution are incubated with 1 μl of inhibitor of appropriate concentration (dissolved in DMSO, pure DMSO solution is used as control) and 5 μl of enzyme solution (conditioned medium). Then 3 μl of the assay mixture are loaded onto an HPTLC plate (silica gel 60, Merck), and the liberated fluorescent dye is separated for detection with an eluent (diethyl ether:petroleum benzine:acetic acid [78:22:1]). After evaporation of the eluent, the plate is read in a fluorescence scanner. An increased liberation of the fluorescent dye in the uninhibited reaction is to be observed as a measure of the enzymic activity.

2.3. Evaluation of the EL-Inhibitory Effect:

The enzymatic activity is reduced as a function of the inhibitor concentration used, and the inhibitor concentration at which a half-maximum enzymatic activity is observed is called $IC_{50}$.

2.4. Further EL Inhibition Assay:

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates the fluorescent dye Bodipy which can be detected after separation by thin-layer chromatography on an HPTLC plate (silica gel 60, Merck) or directly in the reaction vessel by measuring the fluorescence.

The substrate solution is prepared by dissolving 100 μg of 1,2-bis(4,4-difluoro-5,7-dimethyl-4-bora-3a,4a-diaza-s-indacene-3-undecanoyl)-sn-glycero-3-phospho-choline (manufacturer Molecular Probes) in 100 μl of DMSO and taking up in 2.4 mg of tripalmitin (Sigma) in 393 μl of chloroform which comprises 20 mg/ml DOP-choline (1,2-dioleoyl-sn-glycero-3-phosphocholine). 39.3 μl of this lipid mixture are transferred into a fresh reaction vessel, and the solvent is evaporated off. The lipid mixture is dissolved in 4 ml of 200 mM TRIS-HCl, 150 mM sodium chloride, pH=7.4, by sonication twice. The subsequent enzymic reaction takes place at 37° C. for 90 minutes. For this purpose, 20 μl of the substrate solution are incubated with 2 μl of inhibitor of appropriate concentration (dissolved in 10% DMSO, using 10% strength DMSO solution for control) and 2 μl of enzyme solution (conditioned medium). The 4 μl of the assay mixture are loaded onto an HPTLC plate (silica gel 60, Merck), and the liberated fluorescent dye is separated for detection with an eluent (diethyl ether:petroleum benzine:acetic acid [78:22:1]). After evaporation of the eluent, the plate is read in a fluorescence scanner. An increased liberation of the fluorescent dye in the uninhibited reaction is to be observed as a measure of the enzymic activity.

In this assay, the compounds of the examples showed the following $IC_{50}$ values:

| Example | $IC_{50}$ [μM] EL |
|---|---|
| 1 | 0.13 |
| 2 | 0.51 |
| 3 | 0.06 |
| 4 | 0.01 |
| 5 | 0.95 |
| 6 | 0.02 |
| 7 | 0.23 |

Preparation Processes

The compounds of the invention of the general formula I are prepared by methods known per se, e.g. by acylation of substituted or unsubstituted benzooxazol-2-one derivatives II with carbamoyl chlorides III (method A), or in two stages by reacting benzooxazol-2-one derivatives II with phosgene or equivalents such as trichloromethyl chlorocarbonate, ditrichloromethyl carbonate or 4-nitrophenyl chloroformate and further reaction of the resulting benzooxazol-2-onecarboxylic acid derivative with amines IV (method B). For compounds in which R2 is hydrogen, the benzooxazol-2-one derivatives II can also be reacted with the appropriate isocyanates V R1-N=C=O.

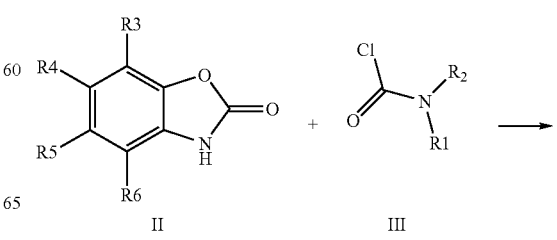

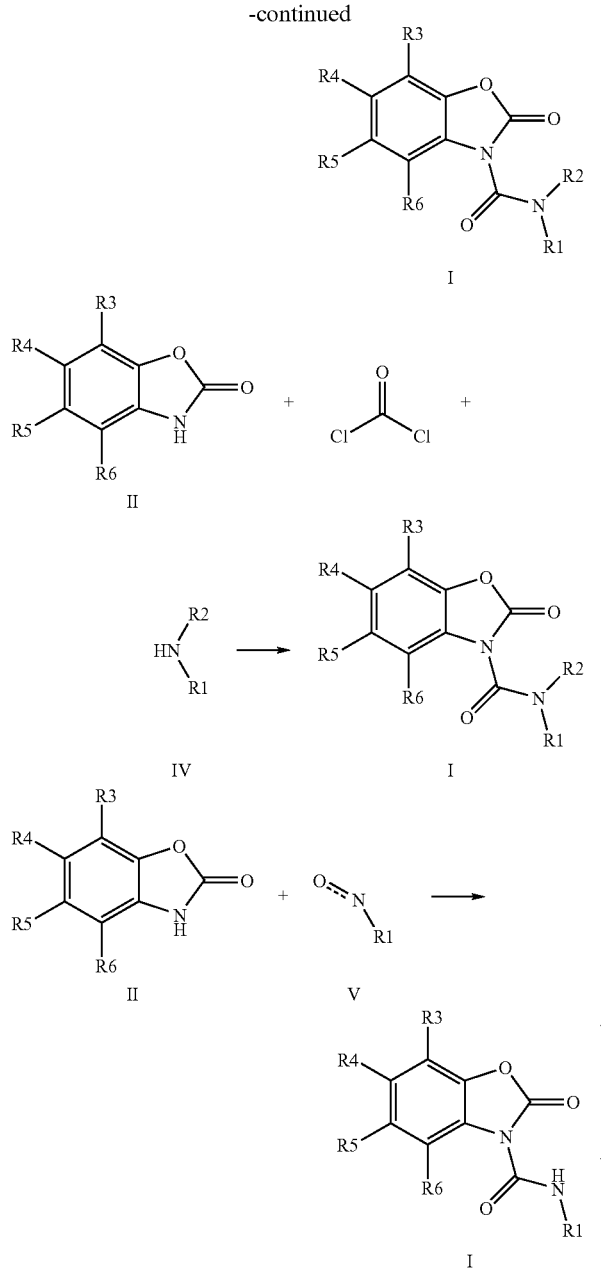

Since acids are usually liberated in these reactions, it is advisable to add bases such as pyridine, triethylamine, sodium hydroxide solution or alkali metal carbonates for expedition. The reactions can be carried out in wide temperature ranges. It has usually proved to be advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are used, strong bases such as lithium hydride, sodium hydride or potassium tert-butoxide in aprotic solvents such as THF or DMF have also proved suitable.

The benzooxazol-2-one derivatives employed as starting compounds II are commercially available or can be prepared by processes known from the literature (e.g. C. Flouzat, Y. Bresson, A. Mattio, J. Bonnet, G. Guillaumet J. Med. Chem. 1993, 36, 497-503; F. Mutterer, C. D. Weis, J. Het. Chem. 1976, 13, 1103-1104).

The examples detailed below serve to illustrate the invention without, however, restricting it.

EXAMPLES

Example 1

6-Acetyl-2-oxobenzooxazole-3-benzylcarboxamide 100 mg (0.565 mmol) of 6-acetyl-3H-benzooxazol-2-one were dissolved in 5 ml of pyridine. Addition of 90.3 mg (0.678 mmol) of benzyl isocyanate was followed by stirring at 80° C. for 5 h, addition of the same amount of benzyl isocyanate once again and stirring at 100° C. for 5 h. The reaction mixture was concentrated and purified by preparative HPLC (PR18, acetonitrile/water 0.1% TFA). Yield: 27 mg (16%), M+H+: 311.1.

Example 2

6-Acetyl-2-oxobenzooxazole-3-(2-methylbenzyl)carboxamide 100 mg (0.565 mmol) of 6-acetyl-3H-benzooxazol-2-one were reacted in analogy to Example 1 with 99.8 mg (0.678 mmol) of 2-methylbenzyl isocyanate. Yield: 63 mg (34%), M+H+: 325.15.

Example 3

6-Acetyl-2-oxobenzooxazole-3-hexylcarboxamide 100 mg (0.565 mmol) of 6-acetyl-3H-benzooxazol-2-one were reacted in analogy to Example 1 with 86.2 mg (0.678 mmol) of 1-isocyanatohexane. Yield: 77 mg (45%), M+H+: 305.15.

Example 4

5-Chloro-2-oxobenzooxazole-3-hexylcarboxamide 100 mg (0.59 mmol) of 5-chloro-3H-benzooxazol-2-one were reacted in analogy to Example 1 with 112.6 mg (0.885 mmol) of 1-isocyanatohexane in the presence of ethyldiisopropylamine in THF at 70° C. Yield: 125 mg (71%), M+H+: 297.1.

Example 5

2-Oxobenzooxazole-3-(2-methylbenzyl)carboxamide 100 mg (0.74 mmol) of 3H-benzooxazol-2-one were reacted in analogy to Example 1 with 130.7 mg (0.888 mmol) of 1-isocyanatomethyl-2-methylbenzene in dioxane at 60° C. Yield: 76 mg (36%), M+H+: 283.25.

Example 6

2-Oxobenzooxazole-3-hexylcarboxamide 100 mg (0.74 mmol) of 3H-benzooxazol-2-one were reacted in analogy to Example 1 with 113 mg (0.888 mmol) of 1-isocyanatohexane in dioxane at 80° C. Yield: 163 mg (84%), M+H+: 263.13.

Example 7

5-Chloro-2-oxobenzooxazole-3-benzylcarboxamide 100 mg (0.59 mmol) of 5-chloro-3H-benzooxazol-2-one were reacted in analogy to Example 1 with 94 mg (0.7 mmol) of isocyanatomethylbenzene in dioxane at 80° C. Yield: 73 mg (41%), M+H+: 303.05.

What is claimed is:

1. A compound of the formula I

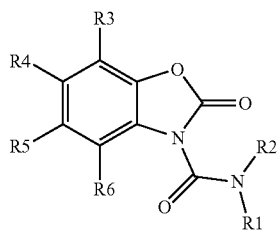

(I)

wherein

R1 is $(C_5-C_{16})$-alkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_3-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

R2 is hydrogen

R3, R4, R5, R6 independently of one another are hydrogen, halogen, $(C_1-C_6)$-alkyl, $(C_1-C_3)$-alkyloxy-$(C_1-C_3)$-alkylene, hydroxy, $(C_1-C_6)$-alkylmercapto, amino, $(C_1-C_6)$-alkylamino, di-$(C_2-C_{12})$-alkylamino, $(C_1-C_6)$-alkylcarbonyl, COOR7, trifluoromethyl, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR9R10 or unsubstituted or mono- or poly-F-substituted $(C_1-C_6)$-alkyloxy;

with the proviso that not more than one of the substituents R3, R4, R5 or R6 is halogen;

and with the proviso that not more than one of the substituents R3, R4, R5 or R6 is $(C_1-C_6)$-alkyl;

R7 is hydrogen, $(C_1-C_6)$-alkyl or benzyl;

and

R9, R10 independently of one another are hydrogen, $(C_1-C_6)$-alkyl, —$(C_6-C_{10})$-aryl, $(C_5-C_{12})$-heteroaryl, $(C_3-C_{12})$-cycloalkyl, $(C_1-C_4)$-alkylene-$(C_6-C_{10})$-aryl, $(C_1-C_4)$-alkylene-$(C_5-C_{12})$-heteroaryl, $(C_1-C_4)$-alkylene-$(C_4-C_{12})$-cycloalkyl or $(C_8-C_{14})$—bicycle; or a tautomer or a physiologically tolerated salt thereof.

2. The compound of the formula I as claimed in claim 1, wherein

R1 is $(C_6-C_{12})$-alkyl, $(C_1-C_3)$-alkylene-$(C_6-C_{10})$-aryl, $(C_1-C_3)$-alkylene-$(C_5-C_{12})$-heteroaryl, $(C_1-C_3)$-alkylene-$(C_4-C_{12})$-cycloalkyl or $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, amino, $(C_1-C_6)$-alkylamino or trifluoromethyl;

R2 is hydrogen;

R3, R4, R5, R6 are independently of one another hydrogen, $(C_1-C_3)$-alkyloxy-$(C_1-C_3)$-alkylene, hydroxy, COOR7, $(C_1-C_6)$-alkylsulfonyl, $(C_1-C_6)$-alkylsulfinyl, aminosulfonyl, pentafluorosulfanyl, $(C_6-C_{10})$-aryl, $(C_5-C_{12})$-heteroaryl, $(C_1-C_6)$-alkylcarbonyl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH or O—CO—$(C_1-C_6)$-alkylene-CO—NR9R10;

R7 is hydrogen, $(C_1-C_6)$-alkyl or benzyl;

and

R9, R10 are independently of one another hydrogen, $(C_1-C_6)$-alkyl, $(C_6-C_{10})$-aryl, $(C_1-C_4)$-alkylene-$(C_6-C_{10})$-aryl.

3. The compound of the formula I as claimed in claim 1, wherein

R1 is $(C_6-C_{12})$-alkyl, benzyl, $(C_1-C_3)$-alkylene-$(C_5-C_{12})$-heteroaryl, $(C_1-C_3)$-alkylene-$(C_4-C_{12})$-cycloalkyl, $(C_8-C_{14})$-bicycle, where aryl, heteroaryl, cycloalkyl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;

R2 is hydrogen;

R3, R4, R5, R6 are independently of one another hydrogen, hydroxy, COOR7, $(C_1-C_6)$-alkylsulfonyl, aminosulfonyl, pentafluorosulfanyl, phenyl, $(C_1-C_6)$-alkylcarbonyl, CO—NR9R10, O—CO—NR9R10, O—CO—$(C_1-C_6)$-alkylene-CO—O—$(C_1-C_6)$-alkyl, O—CO—$(C_1-C_6)$-alkylene-CO—OH or O—CO—$(C_1-C_6)$-alkylene-CO—NR9R10;

R7 is hydrogen or $(C_1-C_6)$-alkyl;

and

R9, R10 are independently of one another hydrogen or $(C_1-C_6)$-alkyl.

4. The compound of the formula I as claimed in claim 1, wherein

R3, R6 are hydrogen; and R4 or R5 is not hydrogen.

5. The compound of the formula I as claimed in claim 1, wherein

R1 is $(C_6-C_{12})$-alkyl, benzyl, —$CH_2$—$(C_5-C_{12})$-heteroaryl, $(C_8-C_{14})$-bicycle, where benzyl, heteroaryl or bicycle may be substituted one or more times by halogen, $(C_1-C_6)$-alkyl, $(C_1-C_3)$-alkyloxy, hydroxy, amino, $(C_1-C_6)$-alkylamino, trifluoromethyl;

R2 is hydrogen;

R3 is hydrogen;

R4, R5 are independently of one another hydrogen, hydroxy, mono-$(C_1-C_6)$-alkylaminocarbonyl, di-$(C_2-C_8)$-alkylaminocarbonyl, COOR7, $(C_1-C_6)$-alkylsulfonyl, aminosulfonyl, phenyl, $(C_1-C_6)$-alkylcarbonyl, O—CO—NR9R10, O—CO—$(C_1-C_6)$-alkylene-CO—O—$(C_1-C_6)$-alkyl, O—CO—$(C_1-C_6)$-alkylene-CO—OH or O—CO—$(C_1-C_6)$-alkylene-CO—NR9R10; and R6 is hydrogen.

6. The compound of the formula I as claimed in claim 1, wherein

R1 is $(C_6-C_{12})$-alkyl or benzyl, where benzyl may be substituted one or more times by $(C_1-C_6)$-alkyl;

R2 is hydrogen;

R3 is hydrogen;

R4, R5 are independently of one another hydrogen, halogen or $(C_1-C_6)$-alkylcarbonyl; and R6 is hydrogen.

7. A pharmaceutical composition comprising one or more compounds of the formula I as claimed in claim 1 or a pharmaceutically acceptable salt thereof or a tautomer thereof in combination with at least one pharmaceutically acceptable excipient.

8. A pharmaceutical composition comprising one or more compounds of the formula I as claimed in claim 2 or a pharmaceutically acceptable salt thereof or a tautomer thereof in combination with at least one pharmaceutically acceptable excipient.

9. A pharmaceutical composition comprising one or more compounds of the formula I as claimed in claim 3 or a pharmaceutically acceptable salt thereof or a tautomer thereof in combination with at least one pharmaceutically acceptable excipient.

10. A pharmaceutical composition comprising one or more compounds of the formula I as claimed in claim 4 or a pharmaceutically acceptable salt thereof or a tautomer thereof in combination with at least one pharmaceutically acceptable excipient.

11. A pharmaceutical composition comprising one or more compounds of the formula I as claimed in claim 5 or a pharmaceutically acceptable salt thereof or a tautomer thereof in combination with at least one pharmaceutically acceptable excipient.

12. A pharmaceutical composition comprising one or more compounds of the formula I as claimed in claim 6 or a pharmaceutically acceptable salt thereof or a tautomer thereof in combination with at least one pharmaceutically acceptable excipient.

13. A method for the treatment of insulin resistance in a patient, which comprises administering to said patient a therapeutically effective amount of a compound of formula I as claimed in claim 1 or a pharmaceutically acceptable salt thereof.

14. A method for the treatment of diabetes mellitus in a patient, which comprises administering to said patient a therapeutically effective amount of a compound of formula I as claimed in claim 1 or a pharmaceutically acceptable salt thereof.

15. A method for the treatment of insulin resistance in a patient, which comprises administering to said patient a therapeutically effective amount of a compound of formula I as claimed in claim 1 or a pharmaceutically acceptable salt thereof and in combination with at least one other active ingredient.

16. A process for preparing compounds of the formula I as claimed in claim 1, which comprises:
   a) acylating benzooxazol-2-one of the formula II with carbamoyl chloride of the formula III;
   or
   b) in two stages reacting benzooxazol-2-one of the formula II first with phosgene or its equivalents chosen from trichloromethyl chlorocarbonate, ditrichloromethyl carbonate or 4-nitrophenyl chloroformate and in a second step reacting with amine of the formula IV;
   in which the substituents are as defined in claim 1:

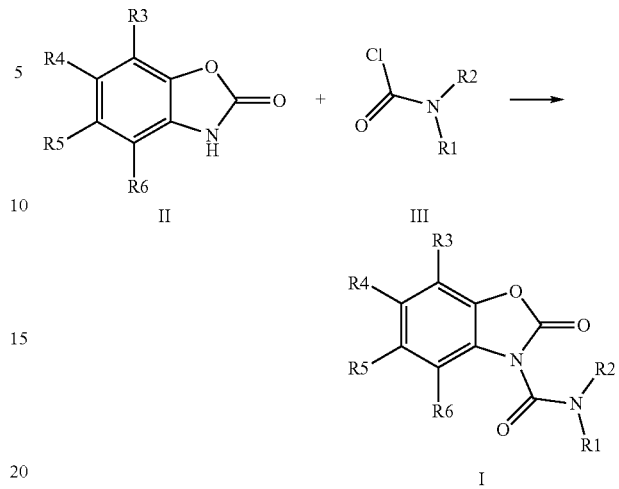

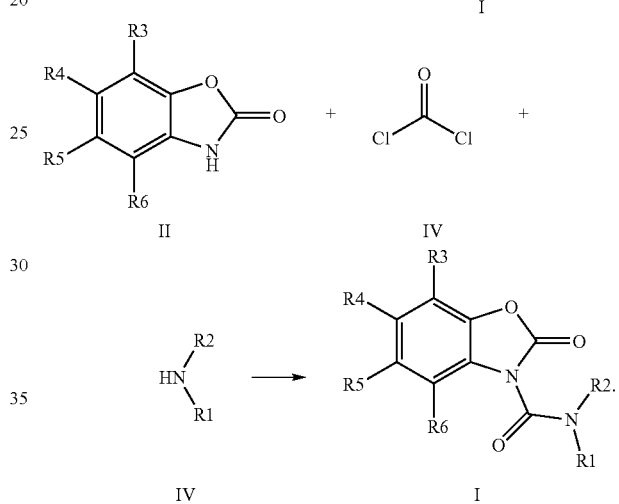

17. A process for preparing compounds of the formula I wherein R2 is hydrogen as claimed in claim 1, which comprises reacting benzooxazol-2-one of the formula II with isocyanates of the formula V: O═C═N—R1:

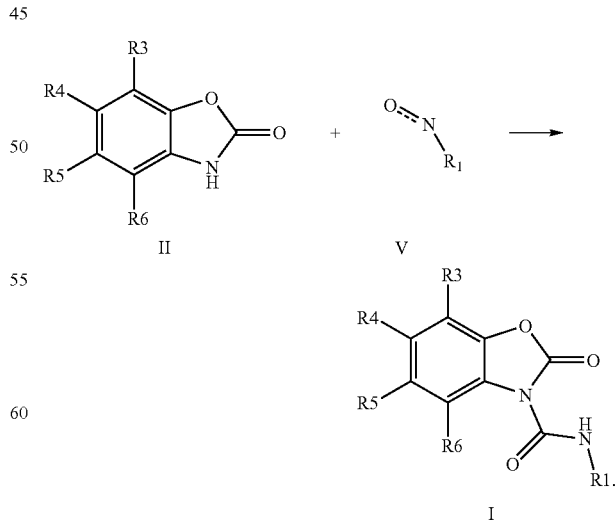

* * * * *

UNITED STATES PATENT AND TRADEMARK OFFICE
CERTIFICATE OF CORRECTION

Page 1 of 1

PATENT NO.        : 7,709,513 B2
APPLICATION NO.   : 11/950960
DATED             : May 4, 2010
INVENTOR(S)       : Gerhard Zoller et al.

It is certified that error appears in the above-identified patent and that said Letters Patent is hereby corrected as shown below:

In column 15, line 21, delete "cannabinoidi" and insert -- cannabinoid --, therefor.

In column 21, line 36, in claim 1, after "hydrogen" insert -- ; --.

In column 21, line 44, in claim 1, delete "CO—NR9R10,O— NR9R10," and insert -- CO—NR9R10, O— NR9R10, --, therefor.

Signed and Sealed this
Twenty-sixth Day of June, 2012

David J. Kappos
*Director of the United States Patent and Trademark Office*